United States Patent [19]

Bochis et al.

[11] 4,250,174

[45] Feb. 10, 1981

[54] 3-SUBSTITUTED IMIDAZO [1,2-A] PYRIDINES

[75] Inventors: Richard J. Bochis, East Brunswick; Peter Kulsa, Plainfield; Richard L. Tolman, Warren, all of N.J.

[73] Assignee: Merck & Co., Inc., Rahway, N.J.

[21] Appl. No.: 35,367

[22] Filed: May 2, 1979

[51] Int. Cl.[3] .................... A61K 31/41; C07D 471/04; C07D 401/02; C07D 403/02
[52] U.S. Cl. .................. 424/248.5; 546/121; 424/256; 424/248.52; 424/250; 544/139; 544/370
[58] Field of Search ............. 546/121; 424/256, 248.5, 424/248.52, 250; 544/139, 370

[56] References Cited

U.S. PATENT DOCUMENTS

| | | | |
|---|---|---|---|
| 3,701,780 | 10/1972 | Fisher | 546/121 |
| 4,096,264 | 6/1978 | Bochis et al. | 546/121 |
| 4,105,767 | 8/1978 | Bochis et al. | 546/121 |
| 4,146,642 | 3/1979 | Bochis et al. | 546/121 |

*Primary Examiner*—Henry R. Jiles
*Assistant Examiner*—Robert C. Whittenbaugh
*Attorney, Agent, or Firm*—David L. Rose; Harry E. Westlake

[57] ABSTRACT

Imidazo pyridines with a carbamate group in the 2-position and a phenylthio, or phenylsulfinyl group in the 6-position are disclosed which also are substituted at the 3-position. The 3-position substituents may be halogen, substituted aminomethyl, acyl, and the like. The compounds are active anthelmintic agents. Compositions and methods for the use of such compounds against helmintic infections are also disclosed.

5 Claims, No Drawings

3-SUBSTITUTED IMIDAZO [1,2-A] PYRIDINES

SUMMARY OF THE INVENTION

This invention is concerned with novel organic compounds which are classified as imidazo [1,2-a] pyridines which are substituted at the 6-position with a phenylthio, or phenylsulfinyl group; the 2-position with a carbamate group and variously substituted at the 3-position, such as with a halogen, substituted or unsubstituted aminomethyl, acyl, and the like. Such compounds are active anthelmintic agents. Thus, it is an object of this invention to disclose novel substituted imidazo [1,2-a] pyridines which have anthelmintic activity. It is a further object of this invention to disclose processes for the preparation of such compounds. A further object is to disclose compositions containing such compounds as the active ingredient for the treatment of helminthiasis. Further objects will become apparent upon reading the following Description of the Invention.

DESCRIPTION OF THE INVENTION

The novel substituted imidazo [1,2-a]pyridines of this invention are best realized in the following structural formula:

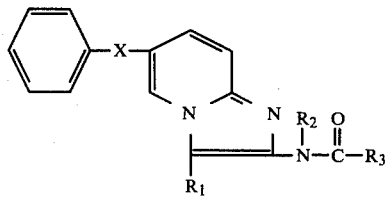

wherein
X is sulfur or sulfinyl;
$R_1$ is halogen, acetyl, haloacetyl, hydroxy methyl, formyl or:

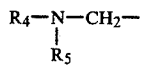

wherein
$R_4$ is hydrogen or loweralkyl and $R_5$ is hydrogen, loweralkyl, hydroxyloweralkyl, carboxyloweralkyl, aminoloweralkyl, mono- or di- (loweralkyl) amino loweralkyl, sulfoloweralkyl, or $R_4$ and $R_5$ may be joined to form a morpholino or N-methyl piperazino ring;
$R_2$ is hydrogen or loweralkyl; and
$R_3$ is loweralkoxy;
Provided that when $R_1$ is chlorine, X is sulfinyl.
In the instant application, the following numbering system is employed for the imidazo [1,2-a] pyridine ring system:

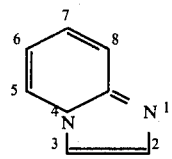

The term "loweralkyl" is intended to include those alkyl groups containing from 1 to 6 carbon atoms of either a straight or branched configuration such as methyl, ethyl, propyl, butyl, amyl, hexyl, isopropyl, tert butyl and the like.

The term "loweralkoxy" is intended to include those alkoxy groups containing from 1 to 6 carbon atoms of either a straight or branched configuration such as methoxy, ethoxy, propoxy, butoxy, amyloxy, hexyloxy, isopropoxy, tert-butoxy, and the like.

The term "sulfo" is used to indicate the "$-SO_3H$" group.

The term "halogen" is intended to include the halogen atoms fluorine, chlorine, bromine and iodine.

PREFERRED EMBODIMENTS OF THE INVENTION

One aspect of the preferred embodiments of this invention is realized in the foregoing structural formula wherein:
X is sulfur or sulfinyl;
$R_1$ is halogen, haloacetyl, formyl or:

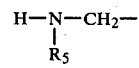

wherein
$R_5$ is hydrogen, loweralkyl, carboxyloweralkyl or sulfoloweralkyl;
$R_2$ is hydrogen or loweralkyl; and
$R_3$ is loweralkoxy;
Provided that when $R_1$ is chloroform, X is sulfinyl.
Further preferred embodiments of this invention are realized wherein:
X is sulfur or sulfinyl;
$R_1$ is bromine, iodine, trifluoroacetyl, formyl or:

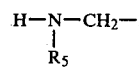

wherein
$R_5$ is hydrogen, methyl, ethyl or sulfoethyl;
$R_2$ is hydrogen; and
$R_3$ is methoxy.
The most preferred compounds are those wherein X is sulfinyl, $R_1$ is bromine or iodine, $R_2$ is hydrogen and $R_3$ is methoxy.

The compounds of this invention are prepared by different processes depending upon the nature of the $R_1$ substituent at the 3-position. The reactions generally utilize as starting material an imidazo [1,2-a] pyridine which has the the appropriate substituents at the 2- and 6-positions. However, in the case of the 6-position substituent, the starting material may be phenylthio, or sulfinyl, or alternatively the starting material could be the phenylthio group, and the sulfoxide could be prepared after the 3-position substituent is prepared. Similarly the $R_2$ group of the starting material could be either hydrogen or loweralkyl, or the $R_2$ group could be hydrogen and the loweralkyl group prepared after the 3-position substituent is prepared. The choice of procedures generally is dependent upon convenience although on occasion, it may be desireable to perform certain steps before others in order to minimize side reactions.

The starting materials for the compounds of this invention are prepared by reacting an appropriately substituted 2-aminopyridine according to the following reaction scheme:

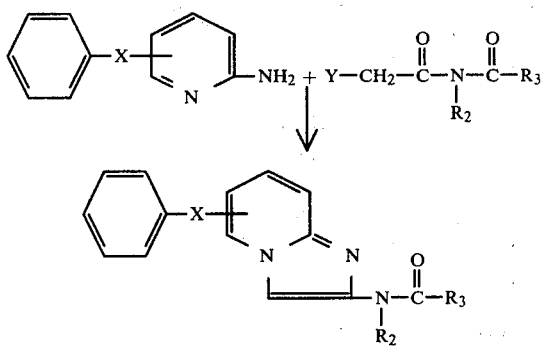

wherein X, $R_2$ and $R_3$ are as previously defined and Y is a halogen selected from chlorine, bromine and iodine. The reactants are combined in a solvent which for optimum results should be a polar aprotic solvent. Suitable solvents are: acetonitrile, dimethylformamide, hexamethylphosphoramide, dimethylacetamide, dimethoxyethane, and the like. The reaction may be conducted at from 50° to 150° C. over a period of from 1 to 50 hours, however, it is preferred to heat the reaction at from 75° to 100° C. for from 1 to 24 hours. The reaction product is isolated by techniques known to those skilled in this art.

The compounds of this invention wherein $R_1$ is a halogen are prepared by halogenating the appropriate 3-unsubstituted compound. The halogenating agent may be a molecular halogen or other halogenating agent, such as N-halo succinimde. For iodinating the starting material, a combination of molecular iodine and a catalytic amount of potassium iodate is preferred. The reaction is carried out generally at room temperature in any solvent non-reactive to the halogenation conditions and non-reactive to the other substituent groups on the imidazo [1,2-a] pyridine substrate. Suitable solvents are carbon tetrachloride, chloroform, tetrahydrofuran, dimethylformamide, benzene, acetic acid and the like. The reaction is generally complete in about 1 to 4 hours. Thin layer chromatography is often used to monitor the reaction to determine when it is completed. If the reaction is not found to have been completed, additional time for reaction, up to about 3 days, is provided.

In the case of those compounds wherein $R_1$ is an acyl group such as acetyl or haloacetyl, such as trifluoroacetyl, the reaction is carried out in an aprotic solvent such as dimethylformamide, tetrahydrofuran and the like. The reaction mixture is heated from about 50° C. to the reflux temperature and is complete in about 1 to 5 hours. The reagents used for the reaction are the anhydrides corresponding to the acyl function of $R_1$ such as acetic anhydride and trifluoroacetic anhydride. Very often it is convenient to dispense with the solvent and use the anhydride reagent as the solvent.

The compounds wherein $R_1$ is formyl are prepared from the 3-unsubstituted imidazo [1,2-a] pyridine and a combination of dimethylformamide and phosphorousoxychloride. The reaction is carried out without a solvent using an excess of the liquid reagents. The dimethylformamide and phosphorousoxychloride are combined and stirred for about 1 hour at room temperature. At the end of this period, the imidazo [1,2-a] pyridine reactant is added portionwise so as to not substantially raise the temperature. The reaction mixture is then stirred at room temperature for 1 to 3 hours. The products are isolated using techniques known to those skilled in this art.

The 3-hydroxymethyl compound is prepared from the 3-formyl compound by reduction. Any reducing agent capable of preparing an alcohol from an aldehyde may be used, however, lithium aluminum hydride in an anhydrous solvent such as tetrahydrofuran is preferred. The reaction is complete in about 1–5 hours at from 0° C. to room temperature.

Another method for the preparation of the 3-hydroxymethyl compound is with a modification of the Mannich reaction described below wherein the 3-unsubstituted compound is reacted with formaldehyde, dimethyl formamide and sodium hydride in the presence of an acid. It has been found preferable to initially react the starting materials and sodium hydride in the dimethyl formamide (usually in excess) at about 75°–125° C. for about 15 minutes to 1 hour. The formaldehyde is then added either as a gas or as paraformaldehyde and the reaction stirred at about room temperature for 2–6 hours. The reaction mixture is then treated with acid, preferably hydrochloric acid and stirred for 10–20 hours at about room temperature. The product is isolated using known techniques.

The compounds wherein $R_1$ is:

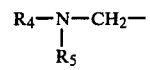

are prepared using Mannich reaction conditions. The reagents used are formaldehyde the H—$NR_4R_5$ amine, and an aqueous or alcoholic acidic solvent. The acid source may be either organic acids, such as acetic acid or mineral acids such as hydrochloric. The concentration of the acid in the water or alcohol may range from dilute to concentrated. When the reaction medium is an aqueous acid, the formaldehyde source is most conveniently an aqueous solution of formaldehyde. When the reaction medium is an alcoholic acid, a formaldehyde source, such as paraformaldehyde is preferred. The formaldehyde or formaldehyde source is present in from 1 to 3 equivalents of the starting material. Additional formaldehyde has not been found to increase yields. The reagents are combined at about 0° C. since occasionally an exothermic reaction is observed on mixing; after this the reaction is stirred at from about 50° to 100° C. for from 1 to 24 hours. Most reactions are complete in from 1 to 4 hours at 50° C. The products are isolated using techniques known to those skilled in this art.

The sulfinyl compounds (wherein X is a sulfoxide) are prepared from the thio compounds (wherein X is sulfur) by oxidation techniques. The oxidation may be carried out either on the imidazo [1,2-a] pyridine starting material, or the oxidation may be carried out after the 3-position substituent is prepared. The oxidation reagents employed may be m-chloroperbenzoic acid, peracetic acid, trifluoroperacetic acid, hydrogen peroxide, and the like. The preferred oxidizing agents are m-chloroperbenzoic acid and peracetic acid. The reaction is generally carried out at room temperature in a solvent inert to oxidation such as chloroform, methylene chloride, benzene, and the like. The reaction is generally complete in from ½ to 3 hours.

When the imidazo [1,2-a] pyridines of this invention are employed for the treatment and control of helminthiasis, the specific means employed for administering the imidazo [1,2-a] pyridines to the animal is not critical and any of the methods now used or available for treating animals infected with or susceptible to infection by helminths are satisfactory. Where it is desired to administer the imidazo pyridine in dry, solid unit dosage form, capsules, boluses or tablets containing desired amount of imidazo pyridine usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of anthelmintic agent depending upon factors such as the type of host animal to be treated, the severity and type of infection and the weight of the host. For large animals such as sheep, swine and cattle, unit dosages up to 15 gm., containing from 1 to 12 gm., of imidazo pyridine, may be employed. It is usually preferred, however, to employ unit dosages weighing from 5 to 10 gm. containing from 2 to 8 gm. of imidazo pyridine. Boluses as well as smaller size tablets contain various binders and lubricants and are compounded by techniques well-known in the art. Capsules are prepared readily by mixing the active ingredient with a diluent such as starch or lactose and filling into the capsule.

In order to treat infected animals by means of a drench, the substituted imidazo pyridines of this invention are mixed with a suspending agent such as bentonite and the solid mix is added to water just prior to administration. Preferred drench formulations contain from about 5 to 50% by weight of the imidazo pyridine.

The imidazo pyridine described herein also may be administered as a component of the feed of the animals of may be dissolved or suspended in the drinking water. Such compositions comprise the imidazo pyridine intimately dispersed in an inert carrier or diluent. By inert carrier, is meant one that will not react with the imidazo pyridine and one that may be administered safely to animals. Preferably, the carrier is one that is, or may be, an ingredient of the animal's ration.

Suitable compositions include feed supplements in which the active ingredient is present in relatively large amounts and which are suitable for addition to the feed either directly or after an intermediate dilution of blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active imidazo pyridines are intimately dispersed throughout the carrier by methods such as grinding, stirring, milling or tumbling. Compositions containing from about 5 to 50% by weight of the imidazo pyridines are particularly suitable as feed additives.

Examples of typical feed supplements containing the imidazo pyridines of this invention dispersed in a solid carrier are:

| | Lbs. |
|---|---|
| (A) | |
| 3-Bromo-2-(methoxycarbonylamino)-6-(phenyl-sulfinyl)imidazo [1,2-a] pyridine | 20 |
| Corn distiller's dried grains | 80 |
| (B) | |
| 3-Iodo-2-(methoxycarbonylamino)-6-phenyl-sulfinyl imidazo [1,2-a] pyridine | 5 |
| Wheat standard middling | 95 |
| (C) | |
| 3-sulfoethyl-2-(methoxycarbonylamino)-6-(phenyl-thio)-imidazo [1,2-a] pyridine | 35 |
| Wheat shorts | 65 |
| (D) | |
| 3-Formyl-2-(methoxycarbonylamino)-6-(phenylthio)-imidazo [1,2-a] pyridine | 50 |
| Corn distiller's grains | 50 |

These and similar feed supplements are prepared by uniformly mixing the imidazo pyridine with the carrier.

Such supplements are added to the animal feed in an amount to give the finished feed the concentration of imidazo pyridine desired for the treatment and control of helminthiasis. Although the desired concentration of active compounds will vary depending upon the factors previously mentioned as well as upon the particular imidazo pyridine employed, the imidazo pyridine compounds of this invention are usually fed at concentrations of between 0.5 to 2.0% in the feed in order to achieve the desired anthelmintic result.

The following examples are provided in order that this invention might be more fully understood. The examples are not intended to be limitative of the invention.

EXAMPLE 1

3-Bromo-2-(methoxycarbonylamino)-6-(phenylthio)imidazo [1,2-a]] pyridine

A suspension of 2-(methoxycarbonylamino)-6-(phenylthio) imidazo [1,2-a] pyridine (300 mg., 1 mmole) in 20 ml. of dichloromethane is treated with N-bromosuccinimide (220 mg., 1.24 mmole). The resultant solution is stirred at room temperature for 48 hours. The precipitate is collected by filtration, washed with dichloromethane and dried to yield 3-bromo-2-(methoxycarbonylamino)-6-(phenylthio) imidazo [1,2-a] pyridine m.p. 165°–168° C.

Alternatively, a suspension of 2-(methoxycarbonylamino)-6-(phenylthio) imidazo [1,2-a] pyridine (600 mg., 2 mmole) in 20 ml. of dichloromethane is treated dropwise with 3 ml. of dichloromethane containing 400 mg. of bromine. After 1 hour, the reaction mixture is filtered and the solids are washed and dried to yield 3-bromo-2-(methoxycarbonylamino)-6-(phenylthio) imidazo [1,2-] pyridine m.p. 165°–166° C.

EXAMPLE 2

3-Bromo-2[methyl-N-(methoxycarbonyl)amino]-6-(phenylthio)imidazo [1,2-a]pyridine A solution of 2[methyl-N(methoxycarbonyl)amino]-6-(phenylthio) imidazo [1,2-a] pyridine (2.5 gm., 8.0 mmoles) in 80 ml. of dichloromethane is treated with N-bromo succinimide (1.78 gm., 10.0 mmoles) in one portion. After stirring at room temperature for 1 hour, the reaction mixture is washed with aqueous sodium thiosulfate, and saturated aqueous sodium chloride. The extracts are dried and concentrated to dryness affording crude product. The crude material is purified by chromatography over 100 g. of silica gel and eluted with 20% ethyl acetate, 80% dichloromethane to yield purified 3-bromo-2[methyl-N-(methoxycarbonyl)amino]-6-(phenylthio) imidazo [1,2-a] pyridine m.p. 95°–98° C.

Alternatively, a suspension of the product from Example 1 (935 mg., 2.48 mmoles) in 15 ml. dimethoxyethane is treated with 104 mg. of a 57% oil dispersion of sodium hydride and heated on a steam bath for 30 minutes. After cooling 352 g. of methyl iodide is added and stirred at room temperature for 2 hours. The reaction mixture is poured onto water and filtered. The filter cake is washed with water, dried and chromatographed as above to yield 3-bromo2[methyl-N-(methoxycarbonyl)amino]-6-(phenylthio)imidazo [1,2-a] pyridine.

EXAMPLE 3

3-Iodo-2-(methoxycarbonylamino)-6-(phenylthio)imidazo [1,2-a] pyridine

A suspension of 2-(methoxycarbonylamino)-6-(phenylthio) imidazo [1,2-a] pyridine (600 mg., 2 mmoles), iodine (420 mg., 3.2 mmoles) and potassium iodate (180 mg., 0.8 mmole) in 60% aqueous acetic acid (50 ml.) containing 2 ml. of concentrated sulfuric acid is stirred at room temperature for 48 hours. The solution is diluted with ice water and the pH adjusted to 8 with aqueous sodium bicarbonate. The reaction mixture is extracted with dichloromethane and the dried extracts are evaporated in vacuo to yield 3-iodo-2-(methoxycarbonylamino)-6-(phenylthio) imidazo [1,2-a] pyridine.

EXAMPLE 4

3-(Dimethylaminomethyl)-2-(methoxycarbonylamino)-6-(phenylthio) imidazo [1,2-a] pyridine 2-(Methoxycarbonylamino)-6-(phenylthio) imidazo [1,2-a] pyridine (0.75 gm.) is added to a solution of 50% aqueous dimethylamine (0.215 gm., 37% formaldehyde (0.19 gm.) and acetic acid (0.35 g.) and heated at 50° C. for 3 hours. After cooling, the reaction mixture is diluted with aqueous sodium bicarbonate and the resultant precipitate is collected by filtration. After drying, the crude product is recrystallized from ethyl acetate to yield 3-(dimethylaminomethyl)-2-(methoxycarbonylamino)-6-(phenylthio) imidazo [1,2-a] pyridine m.p. 172°–175° C.

EXAMPLE 5

3-(Morpholinomethyl)-2-(methoxycarbonylamino)-6-(phenylthio) imidazo [1,2-a] pyridine From the reaction of 0.75 g. of 2-(methoxycarbonylamino)-6-(phenylthio) imidazo [1,2-a] pyridine and 0.83 ml. acetic acid, 18 ml. of 37% formaldehyde and 0.216 g. of morpholine, following the procedure of Example 8, there is obtained 3-(morpholinomethyl)-2-(methoxycarbonylamino)-6-(phenylthio) imidazo [1,2-a] pyridine m.p. 158°–182° C.

EXAMPLE 6

Following the procedure of Examples 4 and 5 as outlined in the following reaction scheme, the identified products are obtained:

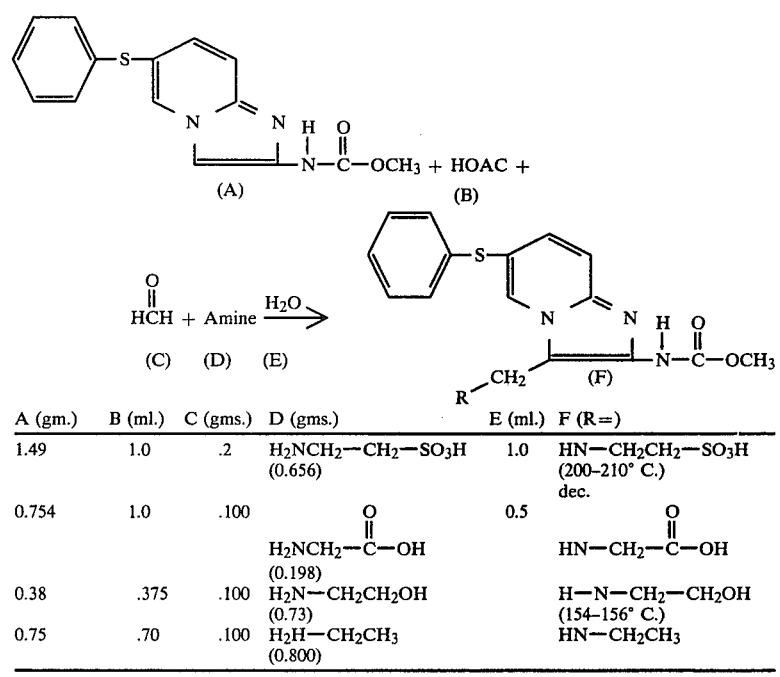

| A (gm.) | B (ml.) | C (gms.) | D (gms.) | E (ml.) | F (R=) |
|---|---|---|---|---|---|
| 1.49 | 1.0 | .2 | H₂NCH₂—CH₂—SO₃H (0.656) | 1.0 | HN—CH₂CH₂—SO₃H (200-210° C.) dec. |
| 0.754 | 1.0 | .100 | H₂NCH₂—C(=O)—OH (0.198) | 0.5 | HN—CH₂—C(=O)—OH |
| 0.38 | .375 | .100 | H₂N—CH₂CH₂OH (0.73) | | H—N—CH₂—CH₂OH (154-156° C.) |
| 0.75 | .70 | .100 | H₂H—CH₂CH₃ (0.800) | | HN—CH₂CH₃ |

EXAMPLE 7

2(Methoxycarbonylamino)-3-trifluoroacetyl-6-(phenylthio) imidazo [1,2-a] pyridine A suspension of 2-(methoxycarbonylamino)-6-(phenylthio) imidazo [1,2-a] pyridine (0.500 gm.) in 10 ml. of trifluoroacetic anhydride is heated at reflux for 2 hours, the reaction mixture is concentrated to dryness and the residue is triturated with aqueous sodium bicarbonate. The product is collected by filtration, washed with water and dried in vacuo. The crude material is purified by recrystallization from ethyl ether to yield 2(Methoxycarbonylamino)-3-trifluoroacetyl-6-(phenylthio) imidazo [1,2-a] pyridine m.p. 171°–173° C.

EXAMPLE 8

3-Acetyl-2-(methoxycarbonylamino)-6-(phenylthio) imidazo [1,2-a] pyridine

A suspension of 2-(methoxycarbonylamino)-6-(phenylthio) imidazo [1,2-a] pyridine (500 mg.) in 10 ml. of acetic anhydride is treated as in Example 7 to yield 3-acetyl-2-(methoxycarbonylamino)-6-(phenylthio) imidazo [1,2-a] pyridine.

EXAMPLE 9

3-Bromo-2-(methoxycarbonylamino)-6-phenylsulfinyl imidazo [1,2-a] pyridine

A suspension of 2-(methoxycarbonylamino)-6-(phenylsulfinyl) imidazo [1,2-a] pyridine is treated with N-bromosuccinimide as in Example 1 to prepare 3-bromo-2-(methoxycarbonylamino)-6-phenylsulfinyl imidazo [1,2-a] pyridine m.p. 150°-152° C.

Alternatively, one may treat a suspension of 3-bromo-2(methoxycarbonylamino)-6(phenylthio) imidazo [1,2-a] pyridine (1.0 gm. 2.64 mmoles) in 100 ml. of dichloromethane with 85% metachloroperbenzoic acid (464 mg., 2.64 mmoles). After 1 hour at room temperature, the solution is washed with aqueous saturated sodium bicarbonate solution, and with water. After drying the solvent is removed in vacuo and the residue is chromatographed over silica gel to yield 3-bromo-2-(methoxycarbonylamino)-6-phenylsulfinyl imidazo [1,2-a] pyridine m.p. 150°-152° C.

EXAMPLE 10

2-(Methoxycarbonylamino)-6-(phenylsulfinyl)-3[2-(sulfoethyl)aminoethyl] imidazo [1,2-a] pyridine A mixture of 2-(methoxycarbonylamino)-6-(phenylsulfinyl) imidazo [1,2-a] pyridine (2.98 g.) 2 ml. of acetic acid, 2 ml. of 37% formaldehyde and 1.3 g. of 2-sulfoethylamine is reacted as described in Example 5 to prepare 2-(methoxycarbonylamino)-6-(phenylsulfinyl)-3[2-(sulfoethyl)aminoethyl] imidazo [1,2-a] pyridine.

EXAMPLE 11

3-Formyl-6-phenylthio-imidazo [1,2-a] pyridine-2-methylcarbonate

A suspension of 2-methoxycarbonylamino-6-phenylthio imidazo [1,2-a] pyridine (6.0 g., 20 mmoles) in dimethylformamide (20 ml.) is stirred with cooling while a cold (10°-20° C.) solution of phosphorous oxychloride (2.3 g., 25 mmoles) in dimethylformamide (7.5 ml.) is added dropwise. The mixture is stirred without cooling for 15 hours. The dark red solution is poured into water, whereupon a solid precipitates. The mixture is neutralized with 38 ml. (95 mmoles) of 5 N potassium hydroxide and heated on a steam bath to 50° C. The hot mixture is filtered, the precipitate washed with water and dissolved in dichloromethane. The dichloromethane solution is washed with water, dried over sodium sulfate and diluted with ethylacetate. Upon concentration in vacuo, crystallization occurs—two crops totaling, 4.88 g.; m.p. of recrystallized material (60.5°-162° C.

EXAMPLE 12

2-(Methoxycarbonylamino)-6-(phenylsulfinyl) imidazo [1,2-a] pyridine

A mixture of 2-(methoxycarbonylamino)-6-(phenylsulfinyl) imidazo [1,2-a] pyridine (1.0 g., 3.17 mmoles), sodium hydride 57% suspension in mineral oil (147 mg., 3.49 mmoles) and 15 ml. of dimethylformamide is heated at 100° C. for 30 minutes. The mixture is cooled to room temperature and formaldehyde gas is bubbled into the reaction mixture with stirring by heating paraformaldhyde (250 mg.) in a separate vessel. The reaction mixture is stirred at room temperature for 4 hours. Hydrochloric acid (12.1 molar, 0.29 ml., 3.49 mmoles) is added and the reaction stirred at room temperature overnight. 150 Ml. of water is added and the precipitated solids removed by filtration. The aqueous filtrate is extracted with methylene chloride which is dried and concentrated to dryness in vacuo. Chromatography on 32 g. of silica gel eluting with 5% methanol in methylene chloride affords 2-(methoxycarbonylamino)-6-(phenylsulfinyl) imidazo [1,2-a] pyridine the structure of which is confirmed by nuclear magnetic resonance and mass spectrometry.

What is claimed is:
1. A compound having the formula:

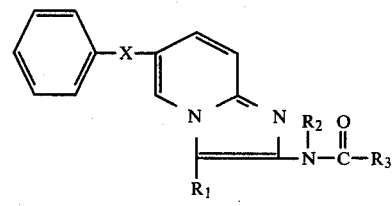

wherein
X is sulfur or sulfinyl;
$R_1$ is, acetyl, haloacetyl, hydroxymethyl, formyl or:

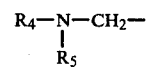

wherein
$R_4$ is hydrogen or loweralkyl; and
$R_5$ is hydrogen, loweralkyl, hydroxyloweralkyl, carboxyloweralkyl, aminoloweralkyl, mono- or di-(loweralkyl) aminoloweralkyl, sulfoloweralkyl, or $R_4$ and $R_5$ may be joined to form a morpholino or N-methyl piperazino ring;
$R_2$ is hydrogen or loweralkyl; and
$R_3$ is loweralkoxy.

2. The compound of claim 1 wherein X is sulfur or sulfinyl; $R_1$ is halogen, haloacetyl, formyl or:

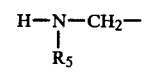

wherein $R_5$ is hydrogen, loweralkyl, carboxyloweralkyl or sulfoloweralkyl; $R_2$ is hydrogen or loweralkyl and $R_3$ is loweralkoxy.

3. The compound of claim 2 wherein X is sulfur or sulfinyl; $R_1$ is bromine, iodine, trifluoroacetyl, formyl or:

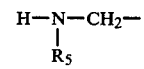

wherein $R_5$ is hydrogen, methyl, ethyl, or sulfoethyl; $R_2$ is hydrogen; and $R_3$ is methoxy.

4. A method for the treatment of helmintic infections which comprises administering to an animal infected with helminths, an effective amount of a compound of claim 1.

5. A composition useful for administration to animals infected with helminths which comprises an effective amount of a compound of claim 1 and an inert carrier.

* * * * *